United States Patent [19]

De Vincentiis

[11] Patent Number: 4,486,437
[45] Date of Patent: Dec. 4, 1984

[54] PHTHALIDYL APOVINCAMINATE WITH CEREBRAL EUBOLIC ACTIVITY

[75] Inventor: Leonardo De Vincentiis, Rome, Italy

[73] Assignee: Ausonia Farmaceutici s.r.l., Pomezia, Italy

[21] Appl. No.: 436,289

[22] Filed: Oct. 25, 1982

[51] Int. Cl.³ ............... A61K 31/435; C07D 461/00
[52] U.S. Cl. ................................. 424/256; 546/51
[58] Field of Search ...................... 546/51; 424/256

[56] References Cited

U.S. PATENT DOCUMENTS 4,035,370 7/1977 Lörincz et al. .................. 546/51

FOREIGN PATENT DOCUMENTS 0893719 11/1982 Belgium .

OTHER PUBLICATIONS

Marzo et al., Arzneim. Forsch., vol. 32(i), pp. 601–603, (Jun. 1982).
Ausonia Farmaceutici, Chemical Abstracts, vol. 98, 126450p, (1983).

Primary Examiner—Donald G. Daus
Assistant Examiner—Diana G. Rivers
Attorney, Agent, or Firm—Bucknam and Archer

[57] ABSTRACT 13a-ethyl-2,3,5,6,13a,13b-hexahydro-1H-indolo (3,2,1-de)pyrido (3,2,1-ij) (1,5) naphthiridin-12-phthalidile carboxylate, having the formula given below, and a procedure for its preparation, are described.

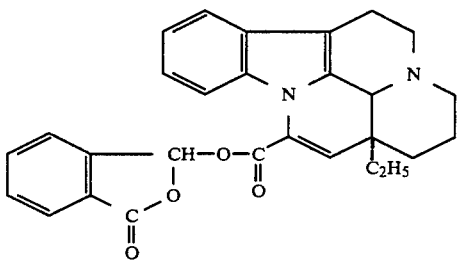

The compound lends itself to the prevention and treatment of cerebrovascular affections and organic and functional syndromes caused by a deterioration of cerebral circulation.

2 Claims, No Drawings

PHTHALIDYL APOVINCAMINATE WITH CEREBRAL EUBOLIC ACTIVITY

The present invention relates to a new vincamine derivative, viz. 13a-ethyl-2,3,5,6,13a,13b-hexahydro-1H-indolo(3,2,1-de)pyrido(3,2,1-ij)(1,5)naphthyridin-12-phthalidyl carboxylate, whose formula (I) is given below:

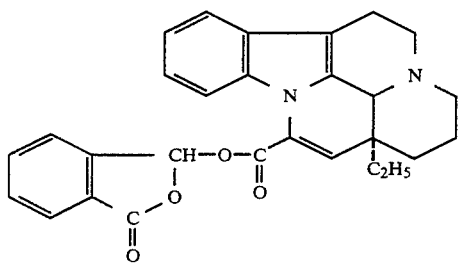

The compound (which can also be defined as phthalidyl apovincaminate and which will hereinafter be referred to as AP 698 for the sake of brevity) has shown itself to be endowed with useful cerebral eubolic properties, enhanced by its low toxicity and favourable pharmacokinetics. Consequently, the invention also relates to pharmaceutical compositions suitable for the treatment of cerebrovascular affections and organic and functional syndromes caused by a deterioration of the cerebral circulation, containing the compound as their active principle.

Further according to the invention, there is provided a process for preparing AP 698, characterised in that bromophthalide (II) is reacted with a metallic salt of apovincaminic acid (III), as follows:

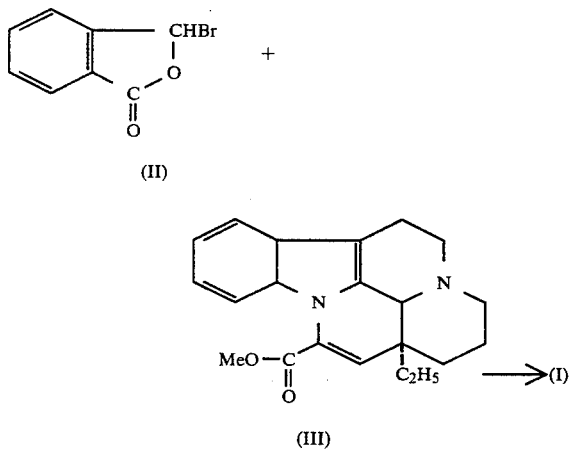

where Me is an alkaline metal, or the equivalent of an alkaline-earth metal.

In a preferred embodiment of the process of the invention, Me is potassium. The reaction is suitably effected in aprotic polar solvents such as dimethylsulphoxide, acetonitrile, dimethylformamide or hexamethylphosphorotriamide, at temperatures of between 0° C. and 60° C., preferably at room temperature.

The example which follows illustrates the process, without limiting the scope of the invention as defined in the appended claims.

EXAMPLE 5 grams (0.0138 mol) of potassium salt of apovincaminic acid are dissolved in N,N-dimethylformamide (40 ml); 3.09 g (0.0138 mol) of bromophthalide and a spatula-tip of potassium iodide, as catalyst, are added. These are left to react at room temperature. The reaction is verified by thin-layer chromatography (eluent: acetate/benzene 70:30). At the end (about 1 hour) the solvent is evaporated, the residue is washed with $H_2O$ and extracted with ethyl acetate. The organic phase is dried, the solvent is evaporated, the ethanol residue is crystallised by hot-filtering with carbon on Celite. This gives 3.35 g (55%) of a crystalline product with a melting point of 190° C., whose analytical data correspond to those calculated for a formula I compound.

Analyses: for $C_{28}H_{26}N_2O_4$ (molecular weight 454.3): Calculated: C=74.00%; H=5.72%; N=6.16%. Found: C=73.83%; H=5.84%; N=6.02%.

The spectral data also confirm the structure of the compound obtained.

Infra-red spectrum in nujol mull: the absorption values of the stretching bands are given in wave number ($cm^{-1}$)

| | | |
|---|---|---|
| Stretching C = O of lactone | 1775 | strong |
| Stretching C = O of ester | 1748 | strong |
| Stretching C = C of alkenes | 1630 | medium |
| Stretching C = C of aromatics | 1600 | medium |
| Stretching C — O two bands | 970 | strong |
| | 960 | strong |

Nuclear magnetic resonance spectrum in $CDCl_3$ with TMS internal standard.

The chemical shift values are given in δ 0.9 (t, 3H, —CH$_2$—CH$_3$); 1.8 (q, 2H, —CH$_2$—CH$_3$); 4.1 (s, 1H, in $C_{13b}$); 6.25 (s, 1H=CH—); 7-8 (m, aromatic 8H, 1H

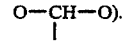

O—CH—O).

The pharmaco-toxicological characteristics of AP 698 can be summarised as follows:

1. TOXICITY

The toxicity of single administrations of AP 698 has been studied in the rat, treating the animals by the oral and intraperitoneal routes with various dosage levels of AP 698.

The LD50 values, determined by the Litchfield and Wilcoxon method (J. Pharmacol. Exp. Therap., 1949, 96, 99) are given in Table 1.

TABLE 1

| | Acute toxicity of AP 698 in the rat. | |
|---|---|---|
| Product | Route of administration | LD50 (mg/kg) (95% confidence limit) |
| AP 698 | p.o. | >3000 |
| | i.p. | 684 (638-720) |

2. PHARMACOLOGICAL PROPERTIES 2.1 Effect on deterioration of electrogenesis by cerebral ischaemia in the rabbit The activity of the product AP 698 has been studied in animals in which ischaemia was induced by occlusion, for 3 minutes and 30 seconds, of the right brachiocephalic truck and the left subclavian artery.

The effects of ischaemia on the cerebrum were therefore shown by EEG, with fronto-occipital derivation, by means of permanent electrodes previously implanted in the appropriate cortical areas of the rabbits and using the "FAT system" described by Borzeix et al (10th Salzburg Conference, 1980).

From all the parameters examined, it emerged that the product AP 698, administered by the intravenous route at the end of the ischaemic manoeuvre, has a dose-dependent therapeutic effect, evident with a dose as low as 0.5 mg/kg (Table II). In the treated animals, in fact, a quicker recovery of the EEG and of the cortical reactivity to stimulation was observed than in the controls and a return in a shorter time to a trace comparable to that recorded in the same animal before the ischaemic manoeuvre.

Quantitative analysis of the traces also made it possible to ascertain that AP 698 is able to eliminate or attenuate a certain number of EEG changes consequent upon the experimental ischaemia and observed during the post-ischaemic phase.

In particular, contrary to that which occurs in the controls, in the animals treated with AP 698 it is noted that:

the frequency of the theta rhythm is not increased, the amplitude is not reduced between the 10th and 20th minutes and the relative representation times are not dispersed.

The beta rhythm is less reduced than in the controls.

The values of the (theta+beta)/(delta+alpha) ratios, between the 14th and the 25th minutes, decrease less than in the controls.

2.2 Changes in mortality caused by hypobaric hypoxia

The experiments were conducted on mice confined in cages in which the pressure was reduced to a level (190 mmHg) which caused the death of the animals.

After determining the survival time of the controls, the effects of various dosage levels of AP 698 were studied.

The results obtained are set out in Table III; these clearly show how the product under examination is able to produce a highly significant extension of the survival time with a substantial protective effect on induced hypobaric hypoxia in the mouse.

2.3 Effect on the smooth musculature

Using the isolated rabbit ileum as an experimental model, AP 698 proved to have considerable myorelaxant activity, decidedly higher than that displayed by vincamine under the same experimental conditions.

This greater effect on the tonus and amplitude of the contractions was found both in the musculature in basal conditions and in the musculature made hypertonic with sodium or serotonin.

TABLE III

Protective effect of AP 698 on mortality from hypobaric hypoxia in the mouse

| Dose (mg/kg i.v.) | Number of animals | Survival time (mean values in sec. ± standard error) | Variation % | Degree of significance (*) |
| --- | --- | --- | --- | --- |
| — | 12 | 72,5 ± 3,5 | — | — |
| 16 | 12 | 67,5 ± 2,5 | −6,9 | N.S. |
| 25,6 | 12 | 116,3 ± 13,5 | +60,4 | 0.01 |
| 41,0 | 12 | 157,9 ± 33,2 | +117,8 | 0.01 |

(*)According to the Mann-Whitney test (1 rank)

3. PHARMACOKINETICS

The pharmacokinetics of enzyme hydrolysis has been studied both in vitro and in vivo in the rat after oral administration of AP 698 labelled with tritium.

The comparisons made showed the following particular kinetic aspects, as against the known ones of vincamine:

(a) Enzyme hydrolysis in vitro determined by incubating AP 698 with rat plasma and measuring the apovincaminic acid formed by gas chromatography gave a half-life of 7.3 minutes.
(b) In vivo tests in the rat have made it possible to find both unchanged AP 698 and apovincaminic acid in the plasma; the half-life of unchanged AP 698 was 72 minutes, while the half-life of the apovincaminic acid which forms in vivo from AP 698 was 7.5 hours.

Thus the presence of persistent levels of apovincaminic acid following the administration of AP 698 can be interpreted as a factor of greater activity and latency, and lower toxicity of AP 698 compared with vincamine.

The compound according to the present invention can be administered by the oral or parenteral route.

Examples of pharmaceutical formulations are as follows:

capsules from 5 mg to 50 mg
tablets from 5 mg to 50 mg
i.m./i.v. ampoules from 5 mg to 15 mg
drops from 1% to 5%

I claim:

1. The compound, 13a-ethyl-2,3,5,6,13a,13b-hexahydro-1H-indolo(3,2,1-de)pyrido(3,2,1-ij)(1,5)naphthyridin-12-phthalidine carboxylate, having the formula

TABLE II

Effect of AP 698 on the post-ischaemic evolution of cerebral electrical activity in the waking rabbit

| | | Time required for the reappearance of: | | | | | | |
| --- | --- | --- | --- | --- | --- | --- | --- | --- |
| | Dose | EEG | | Normal | | Start of | Normal | |
| Product | mg/kg i.v. | Anterior cortex | Posterior cortex | amplitude | Response produced | reactivity | reactivity | Normal trace |
| Controls | — | 1'25" | 1'14" | 25'51" | 25'19" | 8'48" | >60' | >60' |
| AP 698 | 0,25 | 1' | 40" | 19'20" | 21'20" | 18'27" | 19' | >60' |
| | 0,50 | 39" | 29" | 18'53" | 13' | 4' | 25' | 23'30" |
| | 1,00 | 1'8" | 46" | 10'13" | 16'30" | 6'34" | 12'53" | 13'25" |

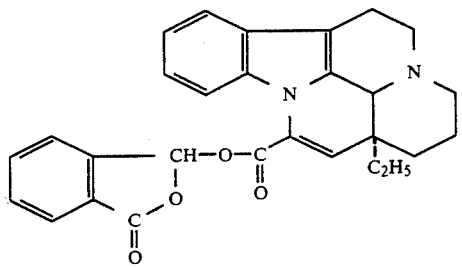 (I)
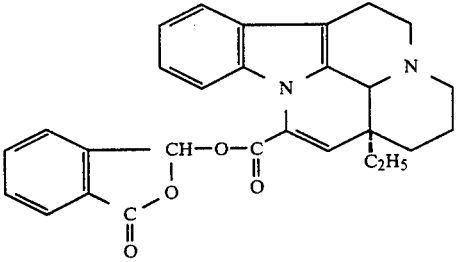 (I)
2. Pharmaceutical compositions in unit dosage form, possessing cerebral eubolic activity, containing the compound as the active principle in an amount of 5-15 mgs per unit or in the form of a 1-5% solution.
* * * * *